United States Patent [19]
Cheong et al.

[11] Patent Number: 5,749,842
[45] Date of Patent: May 12, 1998

[54] WOUND DRESSING PACKAGE

[75] Inventors: Catherine L. Cheong, Burnley; David Rigby, Slough, both of United Kingdom

[73] Assignee: Johnson & Johnson Medical, Inc., Arlington, Tex.

[21] Appl. No.: 293,864

[22] Filed: Aug. 22, 1994

[30] Foreign Application Priority Data

Aug. 31, 1993 [GB] United Kingdom ............... 9318016

[51] Int. Cl.⁶ ............................... A61F 5/00; A61I 17/02
[52] U.S. Cl. .................... 602/41; 602/58; 206/440; 206/441
[58] Field of Search ................ 602/41–58; 128/888, 128/889; 206/438, 439, 440, 441, 812, 459.5; 604/304

[56] References Cited

U.S. PATENT DOCUMENTS

| | | | |
|---|---|---|---|
| 3,624,126 | 11/1971 | Kurtz et al. | 206/63.3 |
| 4,357,935 | 11/1982 | Frantzich et al. | 604/304 |
| 4,915,102 | 4/1990 | Kwiatek et al. | 206/440 X |
| 5,000,172 | 3/1991 | Ward | 602/41 |
| 5,099,832 | 3/1992 | Ward | 602/57 |
| 5,423,737 | 6/1995 | Cartmell et al. | 602/57 |

FOREIGN PATENT DOCUMENTS 887165  1/1962  United Kingdom.
0 341 045 A2  11/1989  United Kingdom.

OTHER PUBLICATIONS

Wound Measurement—An Image Of The Future—Clinica 559, Jul. 7, 1993, p. 17.
European Patent Office Standard Search Report for GBA 9318016.4.

*Primary Examiner*—Richard J. Apley
*Assistant Examiner*—Kim M. Lee
*Attorney, Agent, or Firm*—Andrew C. Farmer

[57] ABSTRACT

There is provided a package for containing a wound dressing, the package comprising a first web and a second web hermetically sealed together around their peripheries, the inside of the package being sterile, wherein the first and second webs include transparent areas which can be superimposed and wherein the internal surface of one of the transparent areas is receptive to marking.

19 Claims, 2 Drawing Sheets

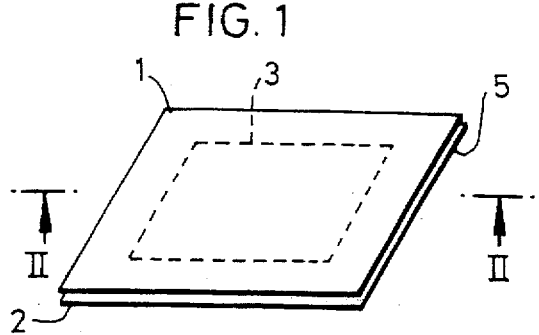
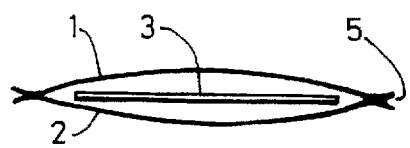
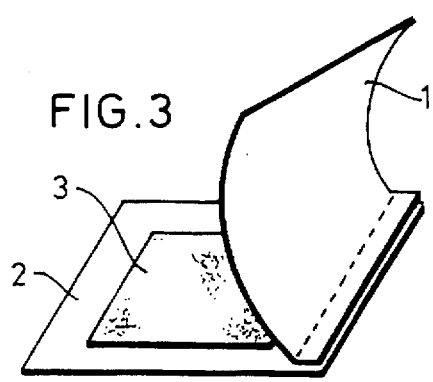
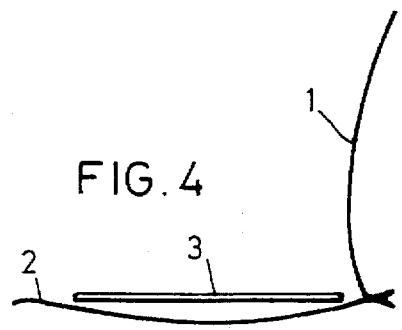
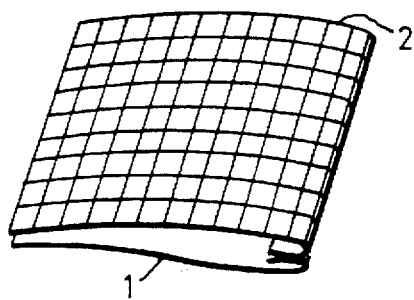
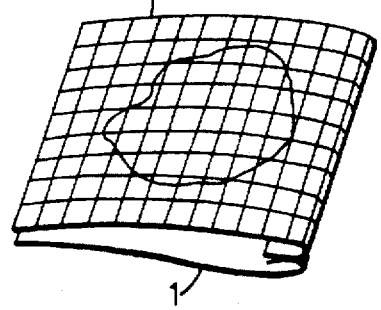
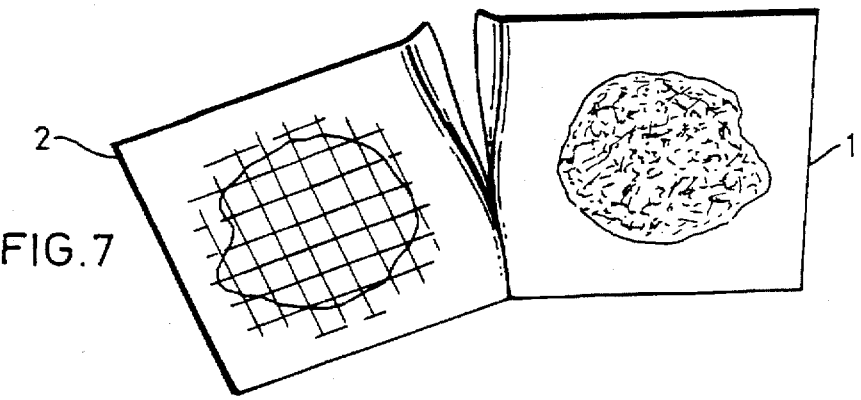

WOUND DRESSING PACKAGE

The present invention relates to a package for a wound dressing and to a method for measuring the area of a wound.

In order to treat wounds, such as cuts, surgical incisions, ulcers and burns, it is generally necessary to apply a dressing to the wound. The dressing serves a number of purposes, one of which is to reduce the risk of the wound becoming infected.

In order to ensure that the dressing itself does not cause wound infection, dressings are generally provided in packaging impermeable to microbes. The dressing and package are sterilized after sealing the package. After transportation to the point of use of the dressing, the inside of the package will still be sterile but the outside of the package will have become contaminated.

It is desirable to be able to monitor the progress of the wound healing process. For instance, the need for wound measurement is referred to in Clinica, 559, 17, 1993. One of the easiest ways to do this is to record details of the wound from time to time. The record may be a picture of the shape of the wound, an estimate of its diameter or an estimate of its area. Each time a record of the wound is made, a note needs to be placed in the patient's record so that a physician can determine whether the wound healing process is progressing at a satisfactory rate.

There are presently available a number of devices which can be used to provide a record of a wound. However, these all suffer from various disadvantages.

A wound measurer was made available by the monthly publication Professional Nurse. The wound measurer comprises a sheet of transparent plastic having marked on one edge a scale in centimeters and in the middle a series of concentric circles of indicated diameter. In order to use this measurer, it is necessary for the user to cleanse one surface to render it sterile. The measurer is then placed with the sterile surface on the wound and an estimate of the diameter of the wound is made. This is then manually entered in the patient's record.

It is disadvantageous to have to cleanse the measurer each time it is used. Also the measurer does not give any idea of the shape of the wound and cannot be placed in the patient's record without being cleansed again.

A wound grid has been used in clinical trials. This comprises a sheet of transparent polyvinyl chloride having a grid of 1 cm squares marked on it. The sheet may also have marked on it areas for recording the patient's name and the date the measurement took place. The sheet is provided in sterile form in a package. In use, the package is opened, the sterile sheet is placed on the wound and an outline is drawn of the wound.

The disadvantages of the wound grid are that it is expensive and that it has to be cleansed after use so that it can be placed in the patient's record. It is also necessary to ensure that one is available at the same time that the dressing is made available.

Smith & Nephew provide a dressing known as OpSite™. This dressing comprises a transparent film. In one form, the OpSite™ film dressing is provided with a transparent sheet on the side of the film remote from the adhesive. The transparent layer has a squared grid marked on it. The film dressing is provided in a sterile package. In use, a release sheet is removed from the adhesive layer and the dressing is adhered to the wound. The wound is then visible through the film layer and the transparent sheet. An outline of the wound and appropriate details are marked on the transparent sheet which is then removed from the film layer and placed in the patient's record.

The disadvantages of this system are that it can only be used with transparent dressings and that it requires an extra layer on the dressing.

The 3M company produces a dressing called Tegasorb™ which is supplied in sterile packaging. On one web of the package there is provided a grid for use in measuring wound size. In use, the gridded web is removed and placed on the wound. An outline of the wound can be marked on this web.

The disadvantages of this system are that it is necessary to ensure that the sterile side of the web is placed on the wound so as to prevent infection and that the web must be cleansed before it can be placed in the patient's records.

Coloplast supply an ulcer dressing in a package having a formed plastic tray for receiving the dressing and a plastic sealing layer. The tray has formed in it a series of concentric circles. If the tray is to be used to measure wound area, it is necessary to cleanse the bottom to render it sterile and then to record the measurement manually. The tray cannot be stored neatly in the patient's record.

The present applicants previously supplied, under the name Dermiflex™, an ulcer dressing in a package having a transparent web on which is marked a series of concentric circles. This web can be used in the same manner as the Tegasorb packaging and has the same disadvantages.

The problem which is addressed by the present invention is that of providing a wound measurement system which overcomes at least to a substantial degree the disadvantages of the prior art systems referred to above.

The present invention in a first embodiment provides a package for containing a wound dressing, the package comprising a first web and a second web hermetically sealed together around their peripheries, the inside of the package being sterile, wherein the first and second webs include transparent areas which can be superimposed and wherein the internal surface of one of the transparent areas is receptive to marking.

The present invention in a second embodiment provides a package for containing a wound dressing, the package comprising a first web and a second web hermetically sealed together around their peripheries, the inside of the package being sterile, wherein: the first web comprises at least two layers which are releasably held together; the inner and outer layers of the first web include transparent areas; and the outer surface of the outer layer of the first web is receptive to marking.

Preferably, the markable area is at least as large in area as the dressing to be contained in the package. Preferably, the markable surface is markable by a permanent marker such as a Pentel™ permanent marker pen.

The first and second webs may be made from separate sheets of the same or different materials. Alternatively, in the first embodiment, the first and second webs may be formed from a single sheet of material, for instance by folding.

Preferably, in the first embodiment, both the first and second webs are completely transparent, except for any product or use information which may be printed on them. Alternatively, one or both of the webs may be opaque or printed around the periphery and have a transparent window.

In the second embodiment, the second web may be opaque, partly opaque or transparent. The two layers in the first web may be held together by electrostatic forces, by heat sealing, by adhesive or by any other suitable means which allows the two layers to be readily separated from each other manually.

Preferably, the markable area has printed on it a grid pattern, advantageously of 1 cm squares. The web including the markable area may, if desired, have printed on or around the markable area record information and spaces to be filled in by the user. Such record information may include; "Patient's name: . . . "; "Date: . . . "; "Doctor: . . . ; and "Nurse: . . . ".

Any suitable material may be used for the webs. Generally, the material(s) will be sterilizable plastics, including polyamides such as nylon, polyesters and polyolefins such as polyethylene or polypropylene. Preferably, the plastics will be a polyester or polyethylene.

Advantageously, the package contains a dressing, the webs are sealed together around the dressing and the dressing is sterile or sterilized after being placed in the package. Preferably, the dressing is placed in the package which is then sealed and sterilized, for instance using gamma irradiation.

Advantageously, the sealing of the package is stronger along one rectilinear line than around the remainder of the dressing. Such a line will be arranged so that one web can be folded around this line and superimposed on the other web. Such a stronger seal may be produced by making the seal wider along one edge than along the other edges.

The dressing may be any presently available wound dressing or any such wound dressing which may in the future become available, including opaque dressings. The nature of the dressing is immaterial to the present invention.

According to a third embodiment of the present invention, there is provided a method for recording the area of a wound which comprises:

providing a wound dressing package according to the first embodiment of the invention;

opening the package;

folding one web onto the other web so that the outer surfaces of the webs are in contact and the transparent areas are superimposed;

placing the folded package on the wound with the markable surface remote from the wound; and marking on the markable surface an outline of the wound.

According to a fourth embodiment of the invention, there is provided a method for recording the area of a wound which comprises:

providing a wound dressing package according to the second embodiment of the invention;

opening the package;

placing the first web on the wound with the markable surface remote from the wound; and marking on the markable area an outline of the wound.

Preferably, the package contains a sterile dressing which, after the opening of the package, is removed. Preferably, once the package is opened, the dressing is placed in a sterile area.

In the third embodiment, once the outline of the wound has been marked, the markable web can be separated from the other web and retained. The other web, which has been in contact with the wound, can be discarded.

In the fourth embodiment, once the outline of the wound has been marked, the marked layer can be separated from the unmarked layer. The unmarked layer, which has been in contact with the wound, can be discarded.

Thus, in both embodiments the user is immediately provided with a record of the wound which can be placed directly into the patient's record.

Before placing marked web into the record, the user may add other marks, such as the name, date, an estimate of the area of the wound, etc.

The advantages of the present invention are that: it does not require any extra packaging or sterilization; it requires no extra space in the secondary packaging to accommodate it; it is sterile and ready to use; it does not require cleaning after use; it can be filed in the patient's record; the marked areas can be compared by overlaying the records and comparing the outlines on the records (thus avoiding the need to quantify the area of the wound); the marked areas are thin and thus will not take up much space in the patient's record; and every dressing is provided with its own individual sterile markable area. Thus, any possible contamination of the wound can be avoided.

Clearly, there is no limit on the size of wound on which the invention can be used. All that is required is the selection of the appropriate size of dressing or combination of dressings. This will automatically have the appropriate size of markable area.

Where the markable area is provided with a grid, the user can not only provide a record of the wound but can also provide an estimate of the area of the wound.

The present invention is now described by way of example only with reference to the accompanying drawings in which:

FIG. 1 is a diagrammatic perspective view of a wound dressing package according to the first embodiment of the present invention;

FIG. 2 is a cross-sectional view along line II—II of FIG. 1;

FIG. 3 is a perspective view of the package of FIG. 1 being prepared for use;

FIG. 4 is a side view of the package of FIG. 3;

FIG. 5 is a perspective view of the package arranged for recording;

FIG. 6 is a perspective view of the package after recording;

FIG. 7 is a perspective view of the package after use; and

Figure 8:
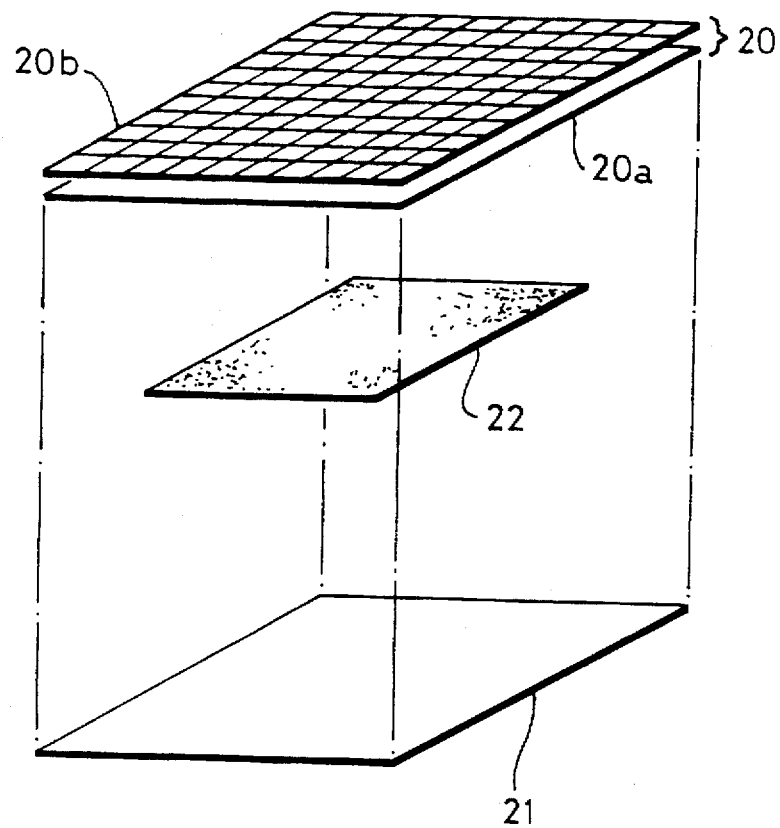
FIG. 8 is an exploded perspective view of a wound dressing package according to the second embodiment of the present invention.

Referring now to FIGS. 1 and 2, a package according to the first embodiment of the present invention comprises a first web 1 and a second web 2 of identical shape and size. Both webs are made of Novaflex™, a nylon/polyethylene web material supplied by DRG Medical Packaging. A wound dressing 3 was placed between the two webs 1, 2. The webs were heat sealed together outside the periphery of the dressing. The seal along edge 5 of the package was along a rectilinear line and was stronger than that along the other three edges. The package and the dressing therein were sterilized by exposure to gamma radiation.

The inside surface of the second web 2 was receptive to marking, for instance using a permanent marker pen, a ballpoint pen, a pencil or a felt-tip pen. The outside surface of the second web 2 also had printed on it a grid of 1 cm squares. If desired, other markings may be printed on the markable surface.

The use of the package is now described with reference to FIGS. 3 to 7. As a first step, the package was opened by breaking the three weaker seals and leaving the stronger seal along edge 5 intact, as shown in FIGS. 3 and 4. The dressing was placed in a sterile field and the first web 1 was folded over so that it underlay the second web 2, as shown in FIG. 5.

The sterile surface of the first web 1 was then at the bottom of the package as shown in FIG. 5. This sterile surface was placed in contact with the wound and the user then marked on the markable surface of the second web 2 an outline of the wound. At the same time, the user marked on the markable area details such as the patient's name and the date the record was made.

Once all the relevant markings had been made, as shown in FIG. 6, the first web 1, which had been in contact with the wound, was separated from the marked second web 2. The first web 1 was discarded and the marked second web 2 was placed directly in the patient's record.

Referring now to FIG. 8, there is shown an exploded view of a package according to the second embodiment of the invention. The package comprised a first web 20 and a second web 21. The first web 20 comprised two layers 20a and 20b. The first and second layers 20a and 20b are transparent and were held together electrostatically. The second layer 20b had a squared grid marked on it. The upper surface (as shown in the drawing) was able to receive marking, for instance using a permanent marker. A dressing 22 was located between the two webs 20, 21. The two webs were heat sealed together around the periphery of dressing 22. The whole package was then sterilized by use of gamma radiation.

In use, the second web 21 was removed and the dressing 22 was placed in the sterile field. The first web 20 was then placed on the wound with the first layer 20a in contact with the wound. The user then marked on the markable surface of the second layer 20b an outline of the wound. At the same time, the user marked on the markable area details such as the patient's name and the date the record was made.

Once all the relevant markings had been made, the first layer 20a was separated from the second layer 20b. The first layer 20a was discarded and the second layer 20b was placed directly in the patient's record.

The present invention has been described above by way of illustration only. The invention is not limited to the specific embodiments described above but encompasses all variations and modifications within the spirit and scope of the invention.

We claim:

1. A package containing a separate sterile wound dressing, the package comprising a first web and a second web hermetically sealed together around their peripheries, each of the first and second webs having an inner surface and an outer surface, said inner surfaces facing each other to define a package interior, said package interior being sterile, wherein each of the first and second webs include transparent areas and wherein the inner surface of one of the first and second webs at the transparent area thereof is receptive to marking and has a grid pattern.

2. The package of claim 1, wherein the first and second webs are formed from a single sheet of material.

3. The package of claim 1, wherein the first and second webs are made from separate sheets of material.

4. The package of claim 3 wherein the material of the first web is different than the material of the second web.

5. The package of claim 1, wherein the the internal surface of the one of the first and second webs at the transparent area thereof which is receptive to marking is at least as large in area as the dressing to be contained in the package.

6. The package of claim 1, wherein both the first and second webs are completely transparent, except for any product or use information which may be printed on them.

7. The package of claim 1, wherein at least one of the first and second webs are not completely transparent around its periphery and has a transparent window.

8. The package of claim 1, wherein the transparent area which is receptive to marking contains a grid pattern.

9. The package of claim 1, wherein the inner surface which is receptive to marking has printed thereon record information and spaces to be filled in by the user.

10. The package of claim 1, wherein the webs are made from sterilizable plastics.

11. The package of claim 1, wherein the sealing of the package is stronger along one rectilinear line than around the remainder of the package.

12. A package containing a separate sterile wound dressing, the package comprising a first web and a second web hermetically sealed together about their peripheries to define a package interior, the package interior being sterile, wherein:

the first web comprises at least two layers which are releasably held together; the layers of the first web include an inner layer and an outer layer; the inner and outer layers of the first web include transparent areas; and the outer layer of the first web has an outer surface which is receptive to marking and has a grid pattern.

13. The package of claim 12, wherein the two layers in the first web are held together by electrostatic forces.

14. A method for recording the area of a wound which comprises:

providing a wound dressing package containing a wound dressing, the package comprising: a first web and a second web hermetically sealed together around their peripheries, each of the first and second webs having an inner surface and an outer surface, said inner surfaces facing each other to define a package interior, said package interior being sterile, wherein each of the first and second webs include transparent areas and wherein the inner surface of one of the first and second webs at the transparent area thereof is receptive to marking;

opening the package;

folding one web onto the other web so that the outer surfaces of the webs are in contact and the transparent areas are superimposed;

placing the folded package on the wound with the markable surface remote from the wound; and marking on the markable surface an outline of the wound.

15. The method of claim 14 wherein the package contains a sterile dressing which, after the opening of the package, is removed.

16. The method of claim 14, wherein once the outline of the wound has been marked, the markable web is separated from the other web and retained.

17. The method of claim 14 wherein, once the outline of the wound has been marked, the marked layer is separated from the unmarked layer.

18. A method for recording the area of a wound which comprises:

providing a wound dressing package containing a wound dressing, the package comprising: a first web and a second web hermetically sealed together about their peripheries to define a package interior, the package interior being sterile, and wherein the first web comprises at least two layers which are releasably held together; the layers of the first web include an inner layer and an outer layer; the inner and outer layers of the first web include transparent areas; and the outer layer of the first web has an outer surface which is receptive to marking;

opening the package;

placing the first web on the wound with the markable surface remote from the wound; and marking on the markable area an outline of the wound.

19. The method of claim 18 wherein the package contains a sterile dressing which, after the opening of the package, is removed.

* * * * *